United States Patent
Blain et al.

(10) Patent No.: US 9,421,020 B2
(45) Date of Patent: Aug. 23, 2016

(54) DRILL GUIDE WITH ROTATING HANDLE

(71) Applicant: Spinal Elements, Inc., Carlsbad, CA (US)

(72) Inventors: Jason Blain, Encinitas, CA (US); Greg Martin, Encinitas, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 127 days.

(21) Appl. No.: 14/286,457

(22) Filed: May 23, 2014

(65) Prior Publication Data

US 2014/0316418 A1    Oct. 23, 2014

Related U.S. Application Data

(63) Continuation of application No. 11/693,145, filed on Mar. 29, 2007, now Pat. No. 8,771,282.

(60) Provisional application No. 60/787,461, filed on Mar. 30, 2006.

(51) Int. Cl.
*A61B 17/17* (2006.01)
*A61B 17/00* (2006.01)

(52) U.S. Cl.
CPC ............. *A61B 17/1728* (2013.01); *A61B 17/17* (2013.01); *A61B 17/1757* (2013.01); *A61B 2017/0046* (2013.01)

(58) Field of Classification Search
CPC ........... A61B 2017/0046; A61B 17/17; A61B 17/1728; A61B 17/1757
See application file for complete search history.

(56) References Cited

U.S. PATENT DOCUMENTS

| | | | |
|---|---|---|---|
| 5,735,855 A | 4/1998 | Bradley | |
| 5,766,221 A * | 6/1998 | Benderev | A61B 17/0401 606/104 |
| 5,984,865 A | 11/1999 | Farley et al. | |
| 6,066,142 A * | 5/2000 | Serbousek | A61B 17/1728 606/70 |
| 6,419,678 B1 * | 7/2002 | Asfora | A61B 17/1757 606/96 |
| 6,506,151 B2 * | 1/2003 | Estes | A61B 17/025 600/226 |
| 6,524,238 B2 | 2/2003 | Velikaris et al. | |
| 6,692,503 B2 | 2/2004 | Foley et al. | |
| 6,699,253 B2 | 3/2004 | McDowell et al. | |
| 7,094,242 B2 | 8/2006 | Ralph et al. | |
| 7,278,997 B1 | 10/2007 | Mueller et al. | |
| 8,771,282 B2 * | 7/2014 | Blain | A61B 17/17 606/86 R |
| 2003/0083667 A1 * | 5/2003 | Ralph | A61B 17/1728 606/96 |
| 2004/0015174 A1 * | 1/2004 | Null | A61B 17/1728 606/99 |
| 2004/0186482 A1 * | 9/2004 | Kolb | A61B 17/1728 606/96 |
| 2004/0204716 A1 | 10/2004 | Fanger et al. | |
| 2005/0015092 A1 | 1/2005 | Rathbun et al. | |
| 2005/0038444 A1 | 2/2005 | Binder et al. | |
| 2005/0228398 A1 * | 10/2005 | Rathbun | A61B 17/1728 606/96 |

* cited by examiner

*Primary Examiner* — Larry E Waggle, Jr.

(74) *Attorney, Agent, or Firm* — Knobbe, Martens, Olson & Bear, LLP

(57) ABSTRACT

A drill guide includes at least one drill guide lumen and a handle coupled to the at least one drill guide lumen. The drill guide lumen includes a proximal opening, a distal opening, and a longitudinal opening therebetween. The handle is movable between a first position relative to the drill guide lumen and a second position relative to the drill guide lumen.

22 Claims, 14 Drawing Sheets

DRILL GUIDE WITH ROTATING HANDLE

CROSS-REFERENCE TO RELATED APPLICATION

The present application is a continuation of U.S. patent application Ser. No. 11/693145, filed Mar 29, 2007. The present application claims priority under 35, U.S.C. §119(e) to the U.S. Provisional Patent Application No. 60/787,461, filed Mar. 30, 2006.

BACKGROUND OF THE INVENTION

1. Field of the Invention

The invention relates generally to systems and methods for performing spinal fixation. Specifically, the invention relates to drill guides, particularly those used for orthopedic procedures.

2. Description of the Related Art

Advancing age, as well as injury, can lead to degenerative changes in the bones, discs, joints, and ligaments of the spine, producing pain and instability. Under certain circumstances, alleviation of the problems can be provided by performing spinal fusion. Spinal fusion is a surgical technique in which two or more vertebrae of the spinal column are fused together to eliminate the motion between the fused vertebrae. Spinal fusion is used to treat conditions where the spine exhibits instability. Spine instability may result from causes such as fracture, scoliosis, and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone fixation systems for treating bone conditions is well established. For example, a bone plate may be positioned over and surrounding the bone injury area and secured to the bone. The bone plate can be secured to the bone by bone screws or other similar fasteners inserted through holes in the bone plate and into the bone itself, sometimes positioned with a drill guide. The screws are tightened so that the bone plate holds the bone to be treated in place in order to insure proper healing. Early fixation devices tended to be applicable only to long-bone injuries, with only limited uses for lower lumbar spinal injuries and disorders. The use of plate/screw fixation systems later expanded, however, to include uses for spinal injuries, including fusion of vertebrae and fixation devices for treating cervical vertebrae injuries.

SUMMARY OF THE INVENTION

In one embodiment, the present invention provides a drill guide comprising at least one drill guide lumen and a handle coupled to the at least one drill guide lumen. The drill guide lumen includes a proximal opening, a distal opening, and a longitudinal opening therebetween. The handle is movable between a first position relative to the drill guide lumen and a second position relative to the drill guide lumen.

The drill guide may further comprise an elongate member including a first end, a second end, and a longitudinal axis therebetween, wherein the at least one drill guide lumen is mechanically coupled proximate to the first end of the elongate member and wherein the handle is mechanically coupled proximate to the second end of the elongate member. The drill guide may further comprise a plurality of drill guide lumens coupled to the handle. The handle may be configured to rotate between the first position and the second position.

The first position may comprise a first angular position of the handle relative to the at least one drill guide lumen and the second position may comprise a second angular position of the handle relative to the at least one drill guide lumen. The handle may be configured with a fixed angular position transverse to the longitudinal opening of the at least one drill guide lumen.

The first position may comprise a first angular position of the handle transverse to the longitudinal opening of the at last one drill guide lumen and the second position may comprise a second angular position of the handle transverse to the longitudinal opening of the at least one drill guide lumen. The handle may be configured with a fixed angular position relative to the at least one drill guide lumen.

The handle may be movably coupled to the at least one drill guide lumen with a locking mechanism. The handle may be movable between the first position and the second position in an unlocked state an immovable between the first position and the second position in a locked state. The locking mechanism may comprise a bushing including a plurality of recesses and a collar disposed around the bushing. The collar may include a flange configured to at least partially fill at least one of the plurality of recesses when the handle is in the locked state. The bushing may be mechanically coupled to the drill guide lumen with a fastener. The plurality of recesses may be configured to permit rotation of the handle in a first direction and may be configured to limit rotation of the handle in a second direction substantially opposite the first direction. The handle may be configured to transition between the locked state when the flange at least partially fills at least one of the plurality of recesses and the unlocked state when the flange does not at least partially fill at least one of the plurality of recesses. The locking mechanism may comprise a threaded lock including a knob and a threaded portion. The threaded portion may be configured to engage a threaded portion of the handle. The threaded portion may be configured to engage a threaded portion of a drill guide lumen extending through the handle. The threaded portion may be configured to engage a threaded portion of the elongate member extending through the handle. The handle may be configured to transition between the locked state and the unlocked state by manipulating a button. The handle may be configured to transition between the locked state and the unlocked state by manipulating a lever, switch or knob.

The first position may comprise a first translational position of the handle relative to the at least one drill guide lumen and the second position may comprise a second translational position of the handle relative to the at least one drill guide lumen. The handle may be configured to slide between the first translational position and the second translational position.

In another embodiment, the present invention provides a method of positioning a drill guide lumen having a longitudinal axis. The method comprises providing a drill guide lumen mechanically coupled to a movable handle, positioning the drill guide lumen with the handle in a first position, and moving the handle from the first position to a second position while the drill guide lumen remains substantially stationary.

Moving the handle may comprise rotating the handle from the first position to the second position, rotating the handle about a pivot point on the drill guide lumen, translationally sliding the handle, and/or manipulating a locking mechanism. The method may further comprise using a drill to insert a bone screw through the drill guide lumen.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

DETAILED DESCRIPTION OF THE PREFERRED EMBODIMENTS

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

As described above, devices such as bone plates or other orthopedic devices can be secured to a bone by bone screws inserted through the device. The insertion of the bone screws may be directed by a drill guide for more precise placement. The drill guide typically comprises a drill guide lumen mechanically coupled to an elongate member, which is mechanically coupled to a handle. The handle provides added maneuverability such that the user may position the drill guide lumen more accurately.

Fixation procedures are often performed by two or more people. In certain embodiments, one user positions the drill guide lumen and the other user operates a drill to insert the bone screws into the bone plate and the bone, guided by the drill guide lumen. However, a handle in a fixed position may impede the ability of the user operating the drill in accessing the drill guide lumen. For example, the handle or the appendages of the user positioning the drill guide may impede access to or visibility of the drill guide lumen, for example by blocking an opening in the drill guide lumen. At least one embodiment of the present invention is the realization that providing a handle movably coupled to the drill guide lumen allows suitable positioning and holding of the drill guide lumen while permitting unimpeded use of the drill.

Figure 1A:
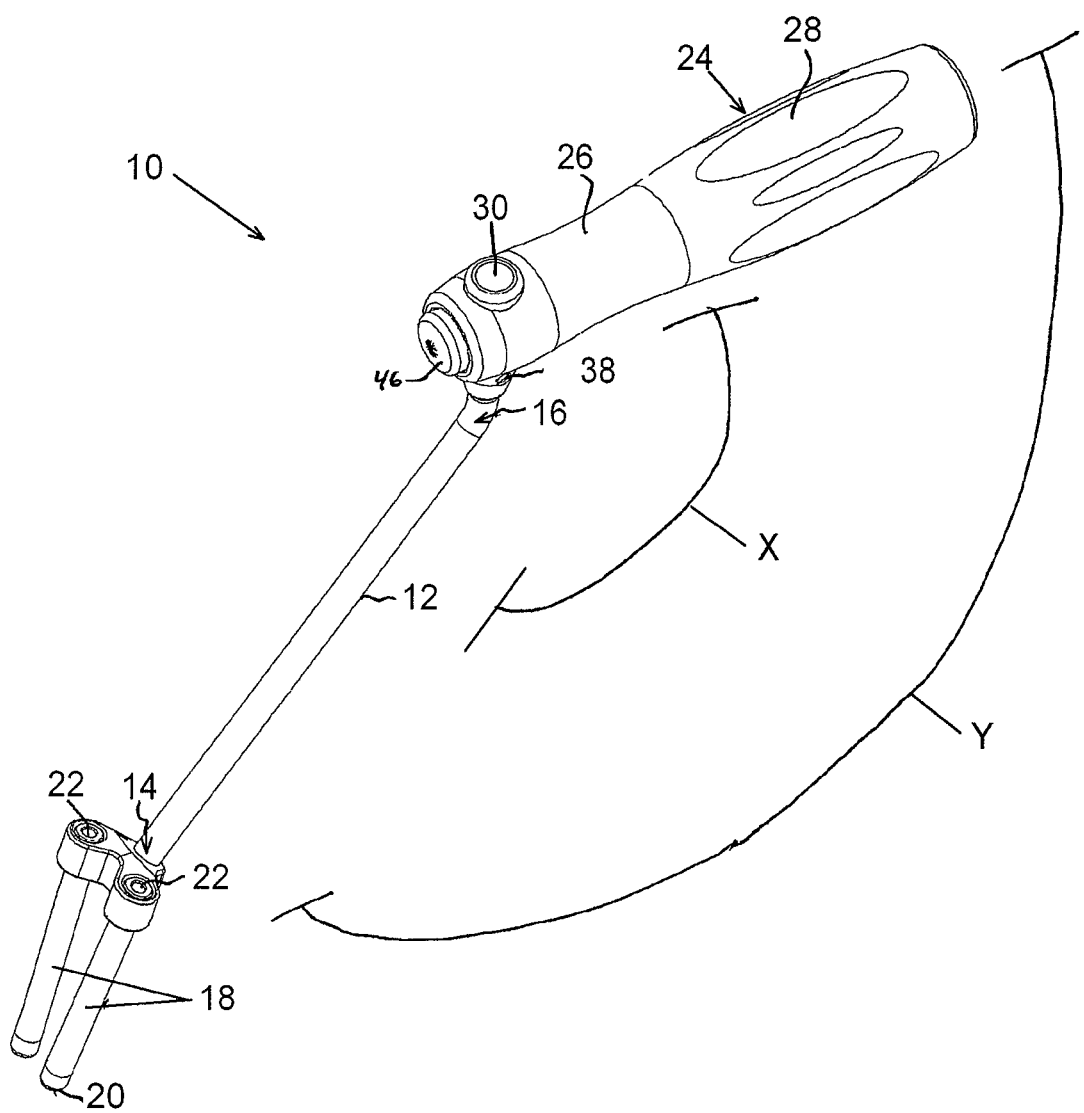
FIGS. 1A through 1C depict a perspective view of one embodiment of a drill guide with a handle in different positions.

FIG. 1A depicts a perspective view of one embodiment of a drill guide 10 with a handle 24 movably coupled to a drill guide lumen 18. The drill guide 10 comprises an elongate member 12 including a first end 14, a second end 16, and a longitudinal axis therebetween. At least one drill guide lumen 18 is coupled proximate to the first end 14 of the elongate member 12. The drill guide lumen 18 includes a proximal opening 22, a distal opening 20, and a longitudinal opening therebetween. It will be appreciated that the drill guide lumen 18 may comprise any shape suitable for accurately guiding a drill kit, including embodiments without an elongate member 12.

Although the embodiment of the drill guide 10 illustrated in FIG. 1A comprises two drill guide lumens 18, the drill guide 10 may comprise any number of drill guide lumens 18 appropriate for the performed procedure. For example, if a procedure requires four bone screws to be inserted into a bone plate, the drill guide 10 may comprise four drill guide lumens 18 such that the bone screws may be inserted into the bone plate and the bone after a single positioning the drill guide, thereby providing greater procedural accuracy for placement of the bone screws. In some embodiments, a drill guide with fewer lumens than the implantable device may be moved about the device after drilling each lumen or sets of lumens.

In some embodiments, the first end 14 of the elongate member 12 is configured to receive any of a plurality of drill guide lumen assemblies. For example, a single drill guide may be able to receive both a drill guide lumen assembly with one drill guide lumen and a drill guide lumen assembly with two drill guide lumens. For another example, a single drill guide would be able to receive both a drill guide lumen assembly with two drill guide lumens arranged in one configuration and a drill guide lumen assembly with two drill guide lumens arranged in another configuration. Suitable assemblies, such as threading and snap-on fittings, are well-known in the mechanical arts.

The drill guide 10 further comprises a handle 24 mechanically coupled proximate to the second end 16 of the elongate member 12 by movable coupling 30. In alternative embodiments, the elongate member 12 is mechanically coupled to the at least one drill guide lumen 18 with a movable coupling, thereby providing a handle 24 movably coupled to the drill guide lumen 18. In certain embodiments, both the mechanical coupling between the drill guide lumen 18 and the elongate member 12 and the mechanical coupling between the elongate member 12 and the handle 24 comprise movable couplings, as described in more detail below. The handle 24 may comprise areas for enhanced gripping, for example a grip area 28 and/or a contour area 26. In some embodiments, the handle 24 is cylindrical. In alternative embodiments, the handle 24 is shaped contoured to a human hand, for example by providing finger and thumb recesses.

Figure 1B:
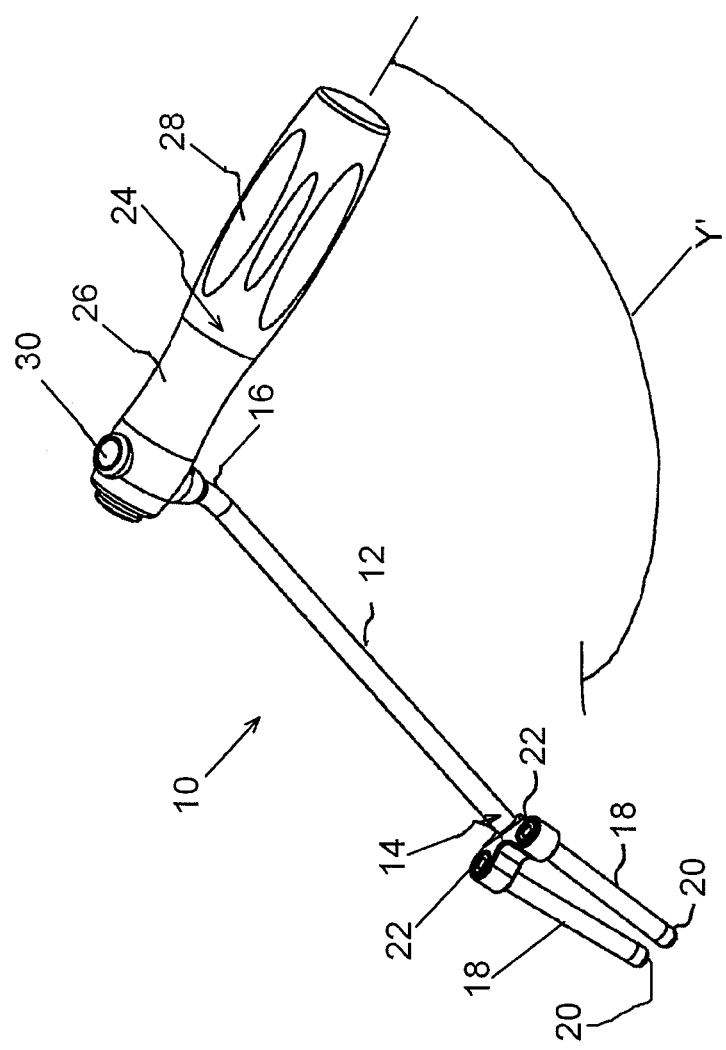
Figure 1C:
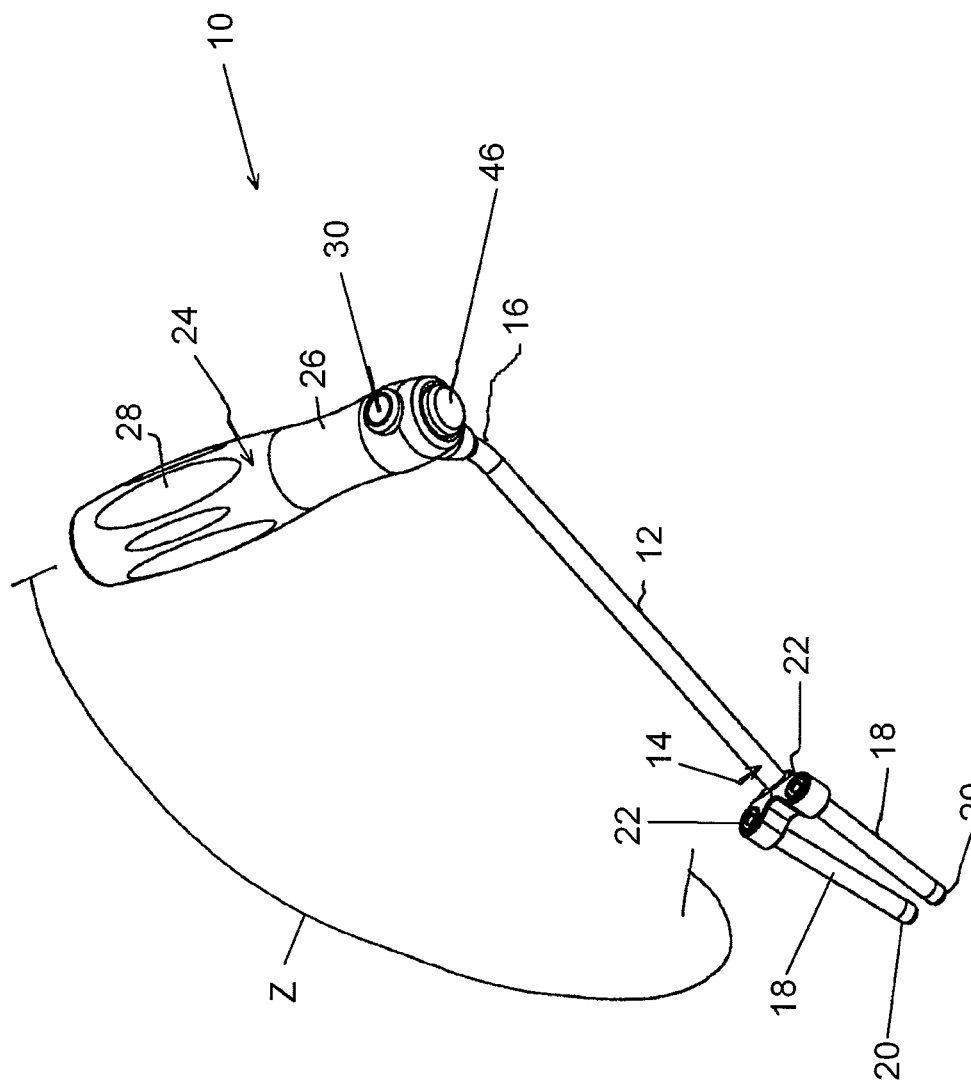

FIG. 1B depicts a perspective view of the drill guide 10 of FIG. 1A with the handle 24 in a different position. The movement of the handle 24 from the position of FIG. 1A to the position of FIG. 1B is described in more detail with respect to the movable coupling 30 below. In some embodiments, the handle 24 is configured to move between the first position of FIG. 1A and second position of FIG. 1B by rotation. The positions of the handle 24 in FIGS. 1A and 1B are provided for illustrative purposes only. For example, FIG. 1C depicts a perspective view of the drill guide 10 of FIG. 1A with the handle 24 in a position different than the positions of FIGS. 1A and 1B. It will be appreciated that the first position may be any position suitable for properly positioning the drill guide lumen 18, and that the second position may be any position suitable for providing secure positioning of the drill guide lumen 18 while also permitting unimpeded access to the drill guide lumen 18. In certain embodiments, the first position of the handle 24 comprises a first angular position relative to the drill guide lumen 18 and the second position of the handle 24 comprises a second angular position relative to the drill guide lumen 18. For example, in the embodiments illustrated in FIGS. 1A and 1B, the first position Y of FIG. 1A is about 90° from the second position Y' of FIG. 1B. For another example, in the embodiments illustrated in FIGS. 1A and 1C, the first position of FIG. 1A is about 90° from the second position of FIG. 1C. For yet another example, in the embodiments illustrated in FIGS. 1B and 1C, the first position of FIG. 1B is about 180° from the second position of FIG. 1C. In some embodiments, the handle 24 is configured to rotate continuously 360° about the movable coupling 30. In other embodiments, rotation may be restricted to a particular movement range.

In certain embodiments, the handle 24 is configured with a fixed angular position transverse to the longitudinal axis of the elongate member 12 or to the drill guide lumen 18. For example, in the embodiment illustrated in FIG. 1A, Angle X between the handle 24 and the elongate member 12 may be approximately a 135° angle. In other positions, the handle 24 would continue to be at approximately a 135° angle transverse to the longitudinal axis of the elongate member 12 or the drill guide lumen 18. The angular position Y relative to the drill guide lumen 18 would change, for example from 0° as depicted in FIG. 1 to 90°, 180°, 270°, or any suitable angle. It will be appreciated that the fixed angular position between the handle 24 and the elongate member 12 or the drill guide lumen 18 may be any angle suitable for positioning the drill guide lumen 18, and that the movable coupling 30 can be adapted to maintain the fixed angular position between the handle 24 and the elongate member 12 or the drill guide lumen 18. In embodiments comprising an elongate member 12 in which the handle 24 is secured at a fixed angular position to the elongate member 12 or to the drill guide lumen 18, the mechanical coupling of the drill guide lumen 18 to the elongate member 12 may be at an angle that compensates for the fixed angular position of the handle 24 transverse to the elongate member 12.

In other embodiments, the handle 24 is movable from a first angular position relative to a pivot point on the longitudinal axis of the elongate member 12 or the drill guide lumen 18 to a second angular position relative to the pivot point on the longitudinal axis of the elongate member 12 or the drill guide lumen 18. For example, a handle 24 may be movable about a pivot point proximate to the second end 16 of the elongate member 12 such that the angular position relative to the longitudinal axis of the elongate member 12 can change from about 135° to 90°, 180°, etc., such that the handle 24 may provide stable positioning of the drill guide lumen 18 while not impeding access to the drill guide lumen 18.

In certain embodiments, the handle 24 is configured with a fixed angular position relative to the drill guide lumen 18. For example, in the embodiment illustrated in FIG. 1A, the handle 24 is secured at approximately a 0° angle from the drill guide lumen 18. In other positions, the handle 24 would continue to be at approximately a 0° angle. The angular position transverse to the longitudinal axis of the elongate member 12 or to the drill guide lumen 18 would change, for example from 135° as depicted in FIG. 1 to 0°, 180°, 360°, or any angle therebetween. It will be appreciated that the fixed angular position between the handle 24 and the drill guide lumen 18 may be any angle suitable for positioning the drill guide lumen 18. In embodiments comprising an elongate member 12 in which the handle 24 is secured at a fixed angular position to the elongate member 12 or to the drill guide lumen 18, the mechanical coupling of the drill guide lumen 18 may be at an angle to compensate for the angle of the fixed angular position of the handle 24 to the elongate member 12 or the drill guide lumen 18.

Figure 2:
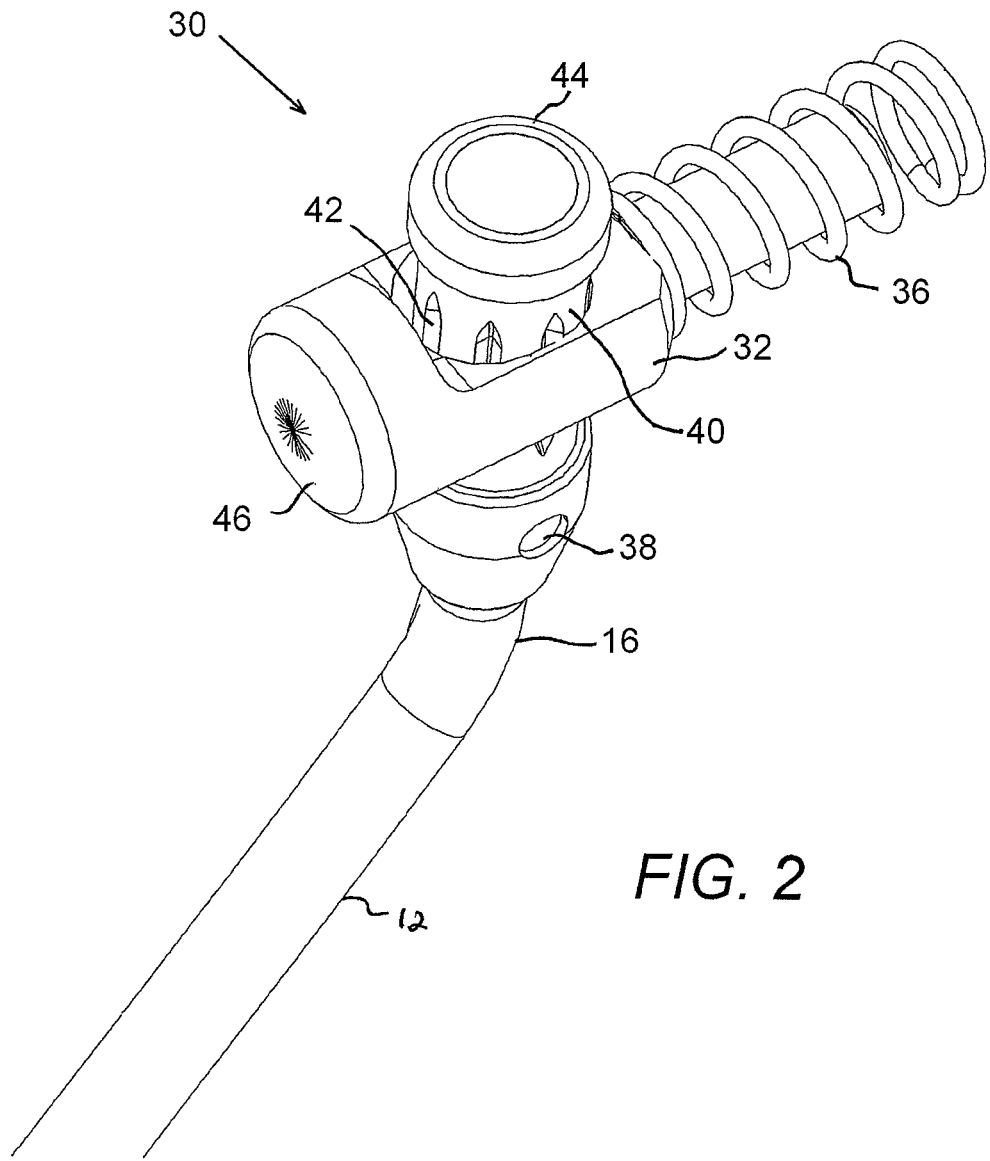
FIG. 2 is an expanded perspective view of one embodiment of a movable coupling.

FIG. 2 depicts an expanded perspective view of one embodiment of a movable coupling 30 in which the handle 24 is movably coupled proximate to the second end 16 of the elongate member 12 or the drill guide lumen 18 with a locking mechanism. The locking mechanism permits the handle 24 to move between a first position and a second position relative to the elongate member 12 or the drill guide lumen 18 in an unlocked state and does not permit movement of the handle 24 relative to the elongate member 12 between the first position and the second position in a locked state (e.g., as depicted in FIG. 2). In the illustrated embodiment, the movable coupling 30 comprises a bushing 40 mechanically coupled proximate to the second end 16 of the elongate member 12 and a collar 32 disposed at least partially around the bushing 40. The movable coupling 30 is secured to the handle 24 by a retaining member 44 connected toward an end of the bushing 40 that provides a stop to prevent the bushing 40 from sliding out from the handle 24 while maintaining rotational movement of the bushing 40.

Figure 3:
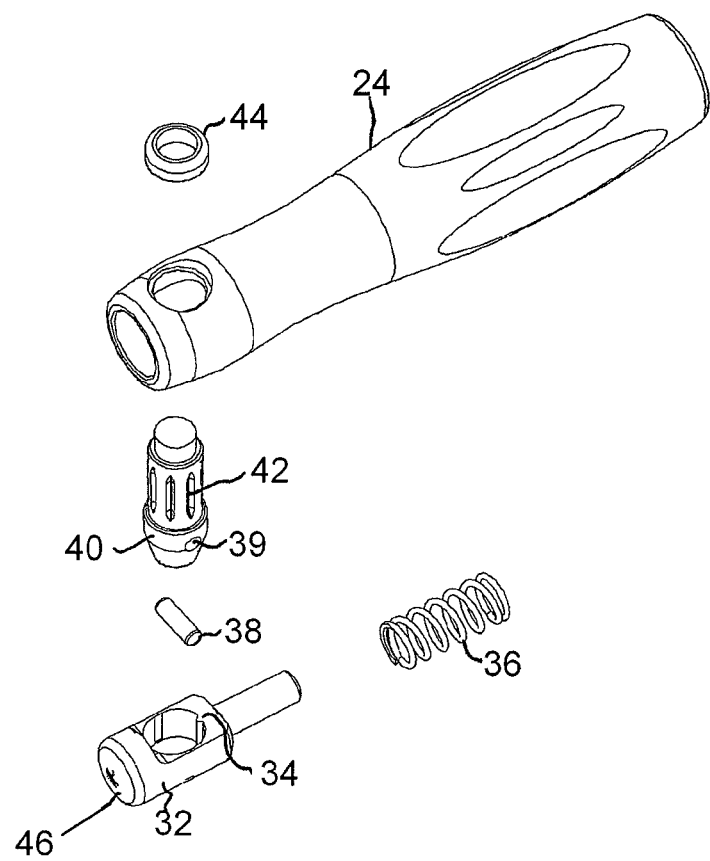
FIG. 3 is a disassembled view of the movable coupling of FIG. 2.
Figure 4A:
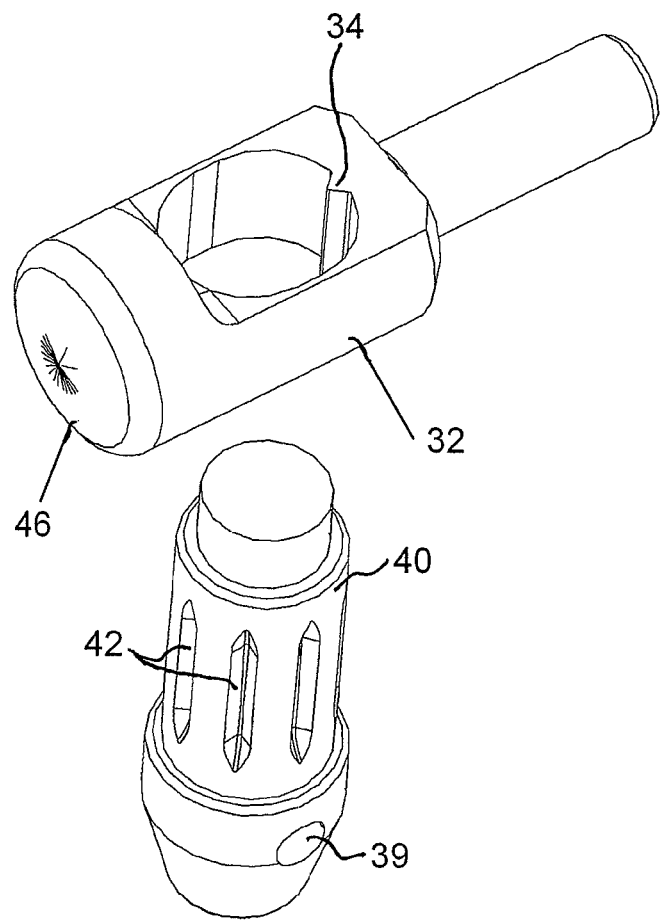
FIG. 4A is an expanded disassembled view of the movable coupling of FIG. 2.
Figures 4B, 4C:
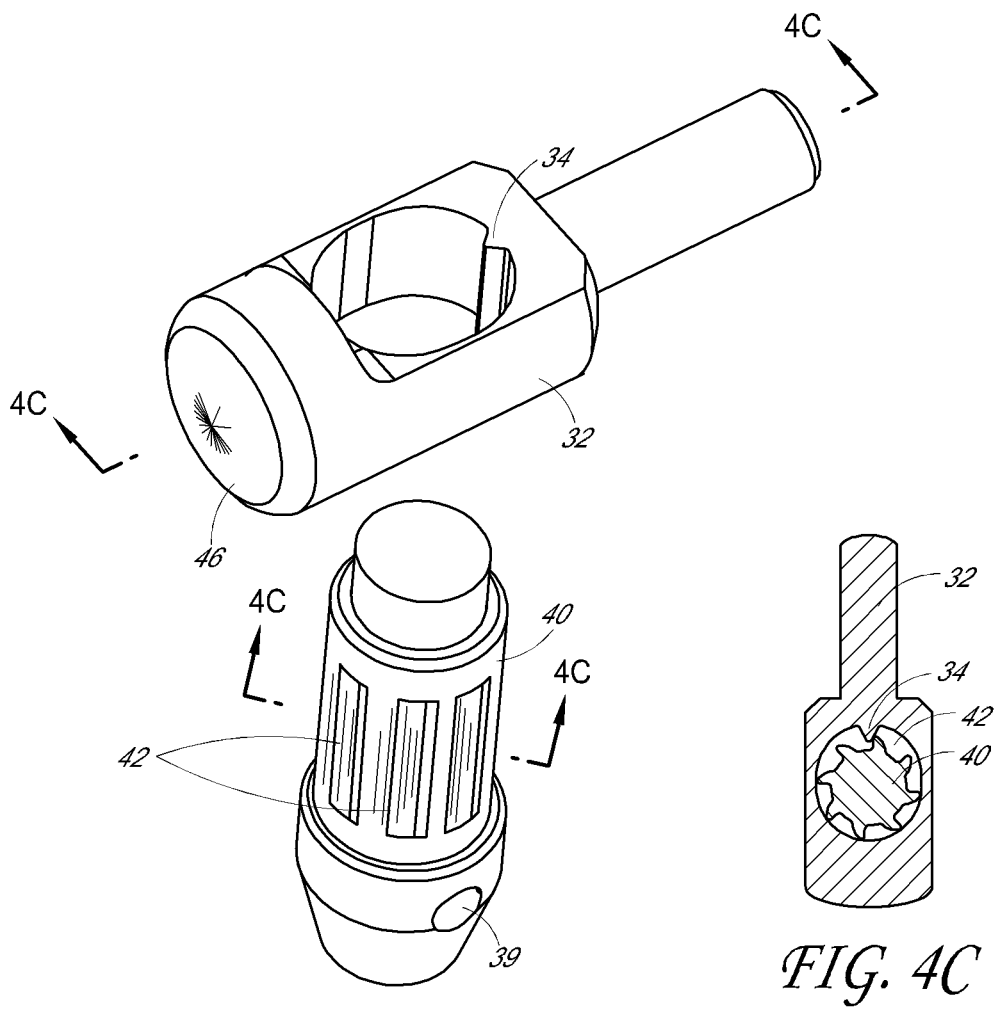
FIG. 4B is an expanded disassembled view of another embodiment of a movable coupling.
FIG. 4C is a cross-sectional view of the components of the movable coupling of FIG. 4B taken along lines 4C-4C.

FIGS. 3 and 4A are disassembled views of the movable coupling 30 of FIG. 2. The bushing 40 comprises a plurality of recesses 42. In some embodiments, the bushing 40 comprises an aperture 39 through which a rivet 38 or any suitable fastening device may mechanically couple the bushing 40 proximate to the second end 16 of the elongate member 12. The collar 32 comprises a flange 34 configured to engage at least one of the plurality of recesses 42 of the bushing 40 when the handle 24 is in a locked state. For example, the illustrated flange 34 of the collar 32 is configured to fit at least partially within at least one of the plurality of recesses 42 of the bushing 40, thereby locking the handle 24 in place. In some embodiments, the plurality of recesses 42 are configured to permit rotation in a first angular direction of the handle 24 and are configured to limit rotation in a second angular direction substantially opposite the first angular direction, such as in a socket wrench system (e.g., as depicted in FIGS. 4B and 4C). In alternative embodiments, the bushing 40 comprises a plurality of flanges and the collar 32 comprises a recess configured to be at least partially filled by at least one of the plurality of flanges. In other alternative embodiments, the bushing 40 and the collar 32 comprise a set of interlocking teeth.

Figure 5A:
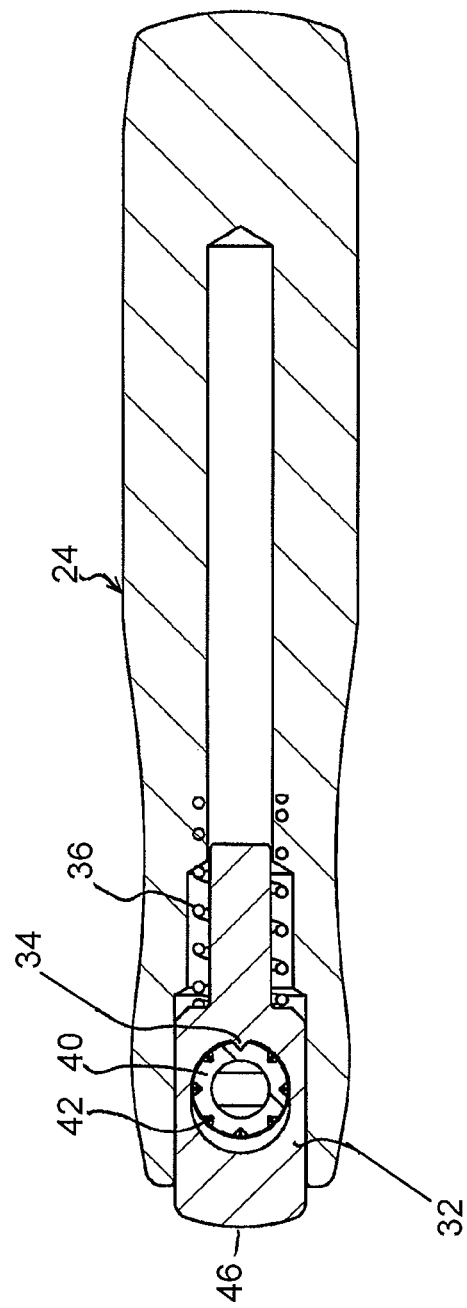
FIGS. 5A and 5B depict a cross-sectional view of one embodiment of a locking mechanism in the locked and unlocked states, respectively.
Figure 5B:
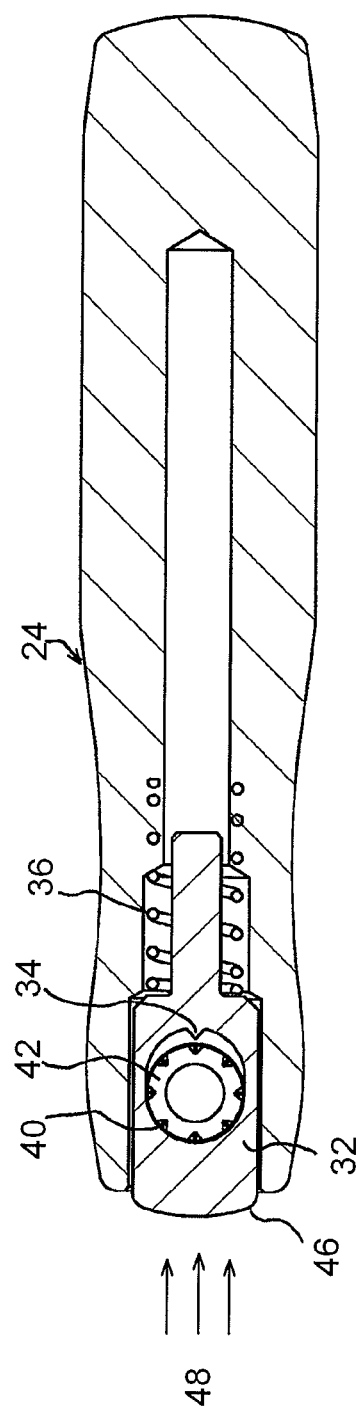

As described above, the handle 24 is configured to be movable between the locked state and the unlocked state when the collar 32 is positioned such that the flange 34 engages and disengages, respectively, at least one of the plurality of recesses 42 of the bushing 40. In one embodiment, the movable coupling 30 further comprises a spring 36 bearing against the collar 32 and a button 46. FIG. 5A illustrates a movable coupling 30 in a locked state wherein the flange 34 at least partially fills at least one of the plurality of recesses 42. In this state, the handle 24 resists movement between a first position and a second position relative to the elongate member 12. FIG. 5B illustrates the movable coupling 30 in an unlocked state with the button 46 engaged (as depicted by arrows 48). When engaged, the button 46 is manipulated to compress the spring 36, causing the collar 32 to move away from the bushing 40, thereby disengaging the flange 34 from the at least one of the plurality of recesses 42 in the bushing 40. In alternative embodiments, the position and spring constant of the spring 36 are reversed such that engaging the button 46 extends the spring 36, causing the collar 32 to move away from the bushing 40, thereby disengaging the flange 34 from the at least one of the plurality of recesses 42 in the bushing 40.

Although the button 46 depicted in FIG. 2 is located at one end of the handle 24, it will be appreciated that the button 46 may be positioned at any suitable location on the handle 24 such that manipulation of it causes the collar 32 to engage and/or disengage with the bushing 40. For example, the button 46 may comprise a wedge positioned on the handle 24 substantially opposite the elongate member 12 that, when vertically manipulated, causes translational movement of the collar 32. It will be appreciated that similar locking and unlocking operation may be achieved by providing a lever or switch rather than a button 46 to engage and disengage the collar 32 from the bushing 40.

As described above, the movable coupling 30 may be provided at the mechanical coupling of the elongate member 12 and the drill guide lumen 18 with similar operation. Rather than the handle 24 moving while the elongate member 12 and the drill guide lumen 18 remain substantially stationary, in such embodiments the handle 24 and the elongate member 12 move while the drill guide lumen 18 remains substantially stationary. Embodiments are also possible in which each of the mechanical couplings comprise a movable coupling such that the handle 24 and the elongate member 12 can move independently while the drill guide lumen 18 remains substantially stationary. In each of the described embodiments, the handle 24 is movable relative to the drill guide lumen 18.

Figure 6A:
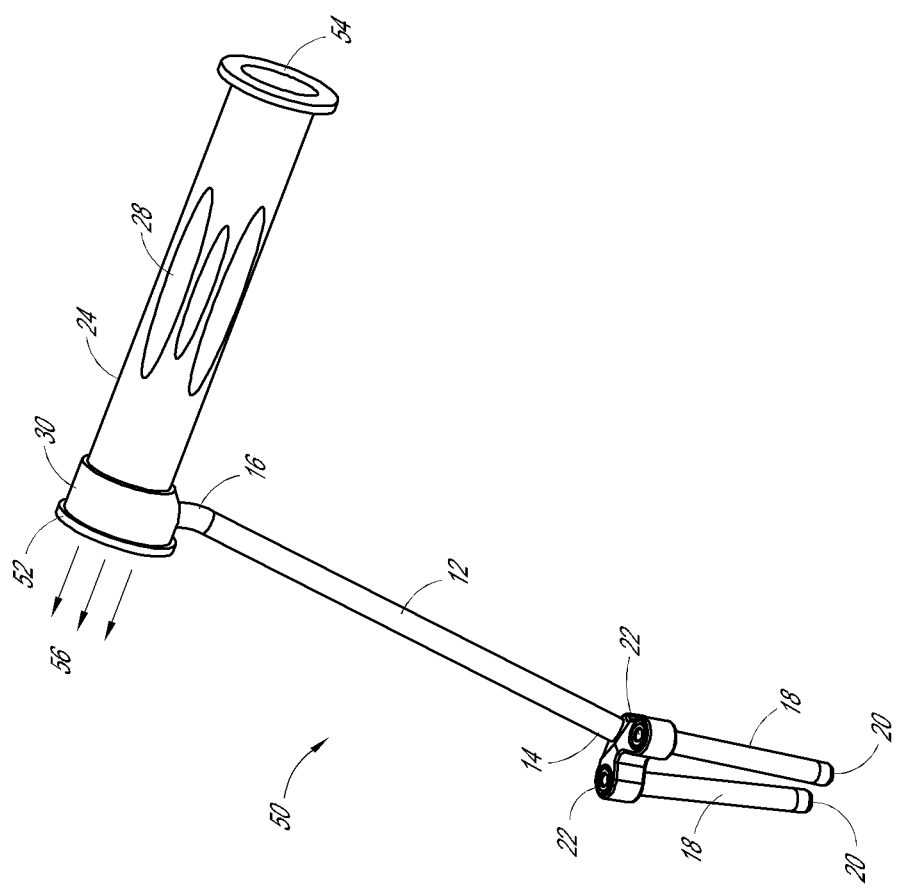
FIGS. 6A and 6B depict a perspective view of another embodiment of a drill guide with a handle in different positions.
Figure 6B:
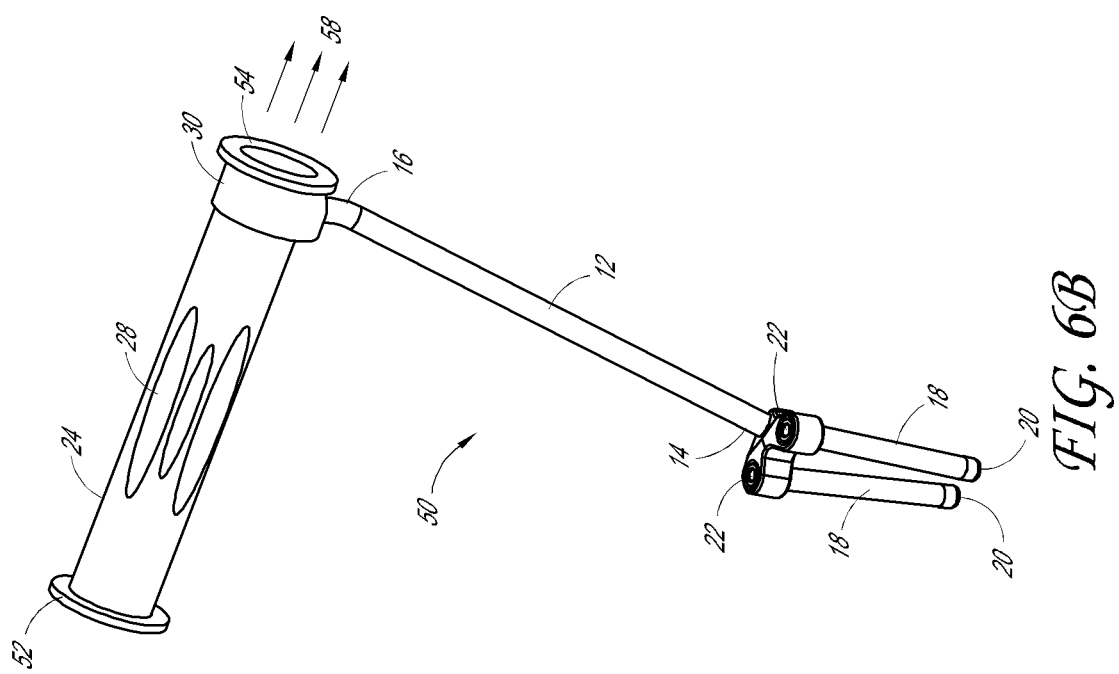

FIG. 6A depicts an embodiment of a drill guide 50. The drill guide 50 comprises a handle 24 configured to slide between a first translational position relative to the drill guide lumen 18 (e.g., as depicted in FIG. 6A) and a second translational position relative to the drill guide lumen 18 (e.g., as depicted in FIG. 6B). The arrows 56, 58 illustrate the direction of movement of the handle 24 between the positions depicted in FIGS. 6A and 6B, respectively. In some embodiments, the handle 24 comprises slide-stops 52, 54 to prevent the handle 24 from fully sliding through the movable coupling 30. In other embodiments, the handle 24 is tapered outwards at the ends to prevent the handle 24 from fully sliding through the movable coupling 30.

Figure 7:
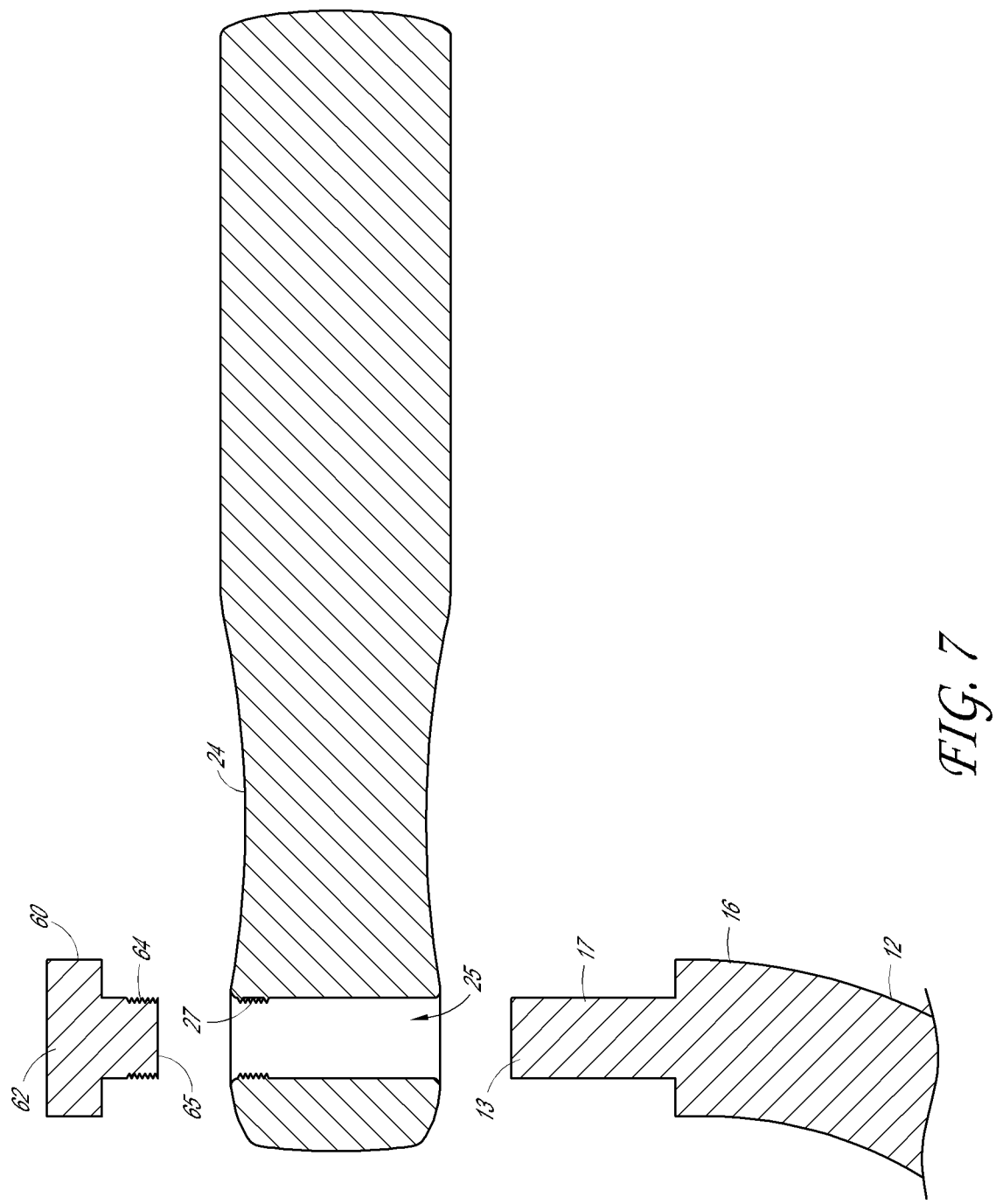
FIG. 7 is a cross-sectional view of the components of yet another embodiment of movable coupling.

FIG. 7 is a cross-sectional view of the components of yet another embodiment of a movable coupling 30. The movable coupling 30 comprises the second end 16 of the elongate member 12, the handle 24, and a threaded lock 60. The second end 16 of the elongate member 12 is shaped such that a hollow area 25 of the handle 24 may fit around the elongate member 12 without sliding down, for example with stepped-in area 17. At least a portion 27 of the hollow area 25 of the handle 24 distal to the elongate member 12 is threaded to engage the threaded lock 60. The threaded lock 60 comprises a knob 62 and a threaded area 64. The threaded area 64 of the threaded lock 60 is adapted to engage the threads of the portion 27 of the hollow area 25 of the handle 24, for example when the knob 62 is turned. When the threaded lock 60 is not engaged, the handle 24 may freely rotate about the elongate member 12. When the threaded lock 60 is engaged (e.g., by being substantially screwed into the hollow area 25 of the handle 24), an edge 65 of the threaded lock 60 bears against the top 13 of the elongate member 12, thereby limiting the rotation of the handle 24. In some embodiments, the edge 65 of the threaded lock 60 and/or the top 13 of the elongate member 12 include teeth, grit, or similar members to enhance effects of the rotation limitation. In some embodiments, a material or layer that enhances the effects of rotation limitation is inserted between the top 13 of the elongate member 12 and the edge 65 of the threaded lock 60. It will be appreciated that the end of the drill guide lumen 18 assembly may be similarly shaped such that rotation of the handle 24 may be limited by a threaded lock 60 without an elongate member 12.

Figure 8:
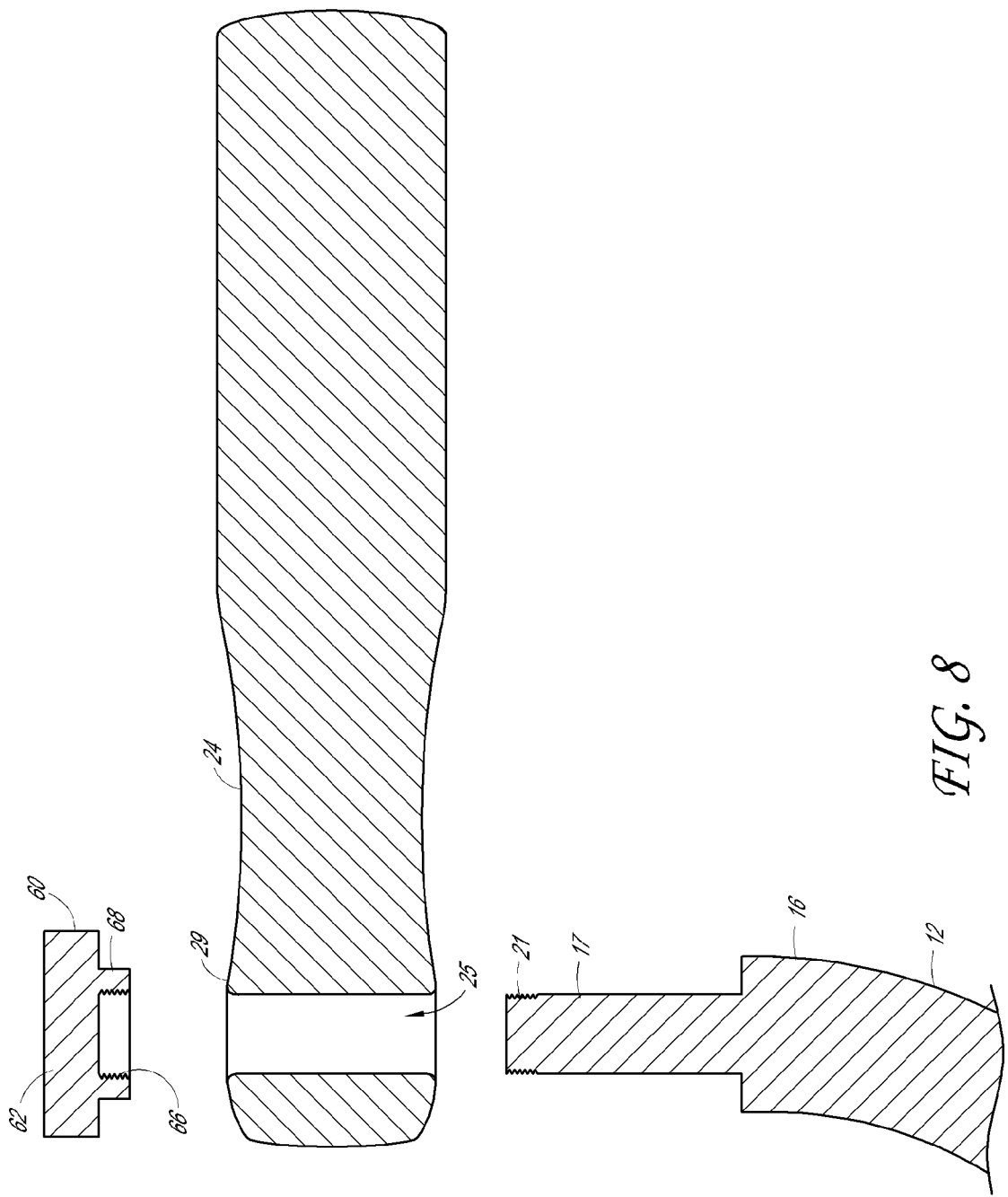
FIG. 8 is a cross-sectional view of the components of still another embodiment of movable coupling.

FIG. 8 is a cross-sectional view of the components of still another embodiment of a movable coupling 30. The movable coupling 30 comprises the second end 16 of the elongate member 12, the handle 24, and a threaded lock 60. The second end 16 of the elongate member 12 is shaped such that a hollow area 25 of the handle 24 may fit around the elongate member 12 without sliding down, for example with stepped-in area 17. At least a portion 21 of the second end 16 of the elongate member 12 is threaded to engage the threaded lock 60. The threaded lock 60 comprises a knob 62 and a threaded area 66. The threaded area 66 of the threaded lock 60 is adapted to engage the threads of the portion 21 of the second end 16 of the elongate member 12, for example when the knob 62 is turned. When the threaded lock 60 is not engaged, the handle 24 may freely rotate about the elongate member 12. When the threaded lock 60 is engaged (e.g., by being substantially screwed onto the second end 16 of the elongate member 12), edges 68 of the threaded lock 60 bears against the top 29 of the handle 24, thereby limiting the rotation of the handle 24. In some embodiments, the edges 68 of the threaded lock 60 and/or the top 29 of the handle 24 include teeth, grit, or similar members to enhance effects of the rotation limitation. In some embodiments, a material or layer that enhances the effects of rotation limitation is inserted between the edges 68 of the threaded lock 60 and the top 29 of the handle 24. It will be appreciated that the end of the drill guide lumen 18 assembly may be similarly shaped such that rotation of the handle 24 may be limited by a threaded lock 60 without an elongate member 12.

Figure 9:
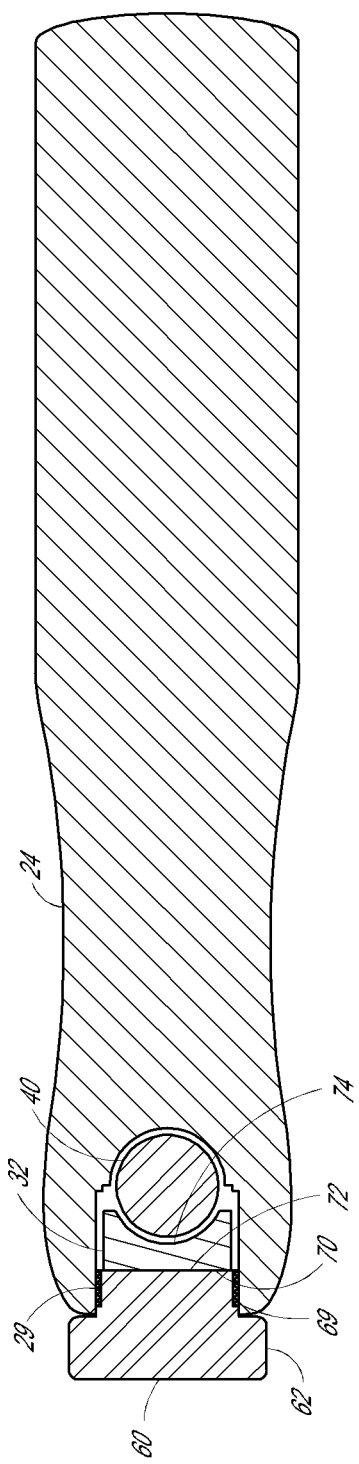
FIG. 9 is a cross-sectional view of yet still another embodiment of a movable coupling.

FIG. 9 is a cross-sectional view of yet still another embodiment of a movable coupling 30. The movable coupling 30 comprises a bushing 40, a collar 32, the handle 24, and a threaded lock 60. At least a portion 29 of the handle 24 is threaded to engage the threaded lock 60. The threaded lock 60 comprises a knob 62 and a threaded area 69. The threaded area 69 of the threaded lock 60 is adapted to engage the threads of the portion 29 of the handle 24, for example when the knob 62 is turned. When the threaded lock 60 is not engaged, the handle 24 may freely rotate about the bushing 40. When the threaded lock 60 is engaged (e.g., by being substantially screwed into the handle 24), the edge 70 of the threaded lock 60 bears against the edge 72 of the collar 32, which causes the edge 74 of the collar 32 to bear against the bushing 40, thereby limiting the rotation of the handle 24. In some embodiments, the edge 70 of the threaded lock 60, the edges 70, 72 of the collar 32, and/or the bushing 40 include teeth, grit, or similar members to enhance effects of the rotation limitation. In some embodiments, a material or layer that enhances the effects of rotation limitation is inserted between the edge 70 of the threaded lock 60 and the edge 72 of the collar 32 and/or between the edge 74 of the collar 32 and the bushing 40.

A method of positioning a drill guide lumen 18 of the embodiments described above comprises positioning the drill guide lumen 18 with the handle 24 in a first position and moving the handle 24 from the first position to a second position while the drill guide lumen 18 remains substantially stationary. In certain embodiments, after positioning the drill guide lumen 18 with the handle 24 in a first position, a button 46 is depressed, thereby disengaging a flange 34 of a collar 32 from a bushing 40 within a movable coupling 30, before the handle 24 is moved to the second position. Once the handle 24 is in the second position, the button 46 is released, thereby allowing the flange 34 of the collar 32 to engage the at least one of the plurality of recesses 42 of the bushing 40. With the handle 24 positioned to not impede the use of a drill, a drill can secure a bone screw through the drill guide lumen 18.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A drill guide comprising:
    at least one drill guide lumen including a proximal opening, a distal opening, and a longitudinal opening therebetween;
    a bushing including a plurality of recesses;
    an elongate member including a first end coupled to the at least one drill guide lumen and a second end coupled to the bushing;
    a collar surrounding the bushing, the collar comprising a flange configured to at least partially fill at least one of the plurality of recesses,
    wherein a handle is movable between a first position relative to the at least one drill guide lumen and a second position relative to the at least one drill guide lumen when the collar is slid to a unlocked state and wherein the handle is immovable between the first position and the second position when the collar is slid to a locked state.

2. The drill guide of claim 1, further comprising a plurality of drill guide lumens coupled to the handle.

3. The drill guide of claim 1, wherein the handle is configured to rotate between the first position and the second position when the collar is slid to the unlocked state.

4. The drill guide of claim 1, wherein the first position comprises a first angular position of the handle relative to the at least one drill guide lumen and the second position comprises a second angular position of the handle relative to the at least one drill guide lumen.

5. The drill guide of claim 4, wherein the handle is configured with a fixed angular position transverse to the longitudinal opening of the at least one drill guide lumen.

6. The drill guide of claim 1, wherein the first position comprises a first angular position of the handle transverse to the longitudinal opening of the at least one drill guide lumen and the second position comprises a second angular position of the handle transverse to the longitudinal opening of the at least one drill guide lumen.

7. The drill guide of claim 6, wherein the handle is configured with a fixed angular position relative to the at least one drill guide lumen.

8. The drill guide of claim 1, wherein the bushing is mechanically coupled to the elongate member with a fastener.

9. The drill guide of claim 1, wherein the plurality of recesses permit rotation of the handle in a first direction and limit rotation of the handle in a second direction substantially opposite the first direction.

10. The drill guide of claim 1, wherein in the locked state the flange at least partially fills at least one of the plurality of recesses and in the unlocked state the flange does not at least partially fill at least one of the plurality of recesses.

11. The drill guide of claim 1, wherein the collar is configured to transition between the locked state and the unlocked state by manipulating a button.

12. The drill guide of claim 1, wherein the collar is configured to transition between the locked state and the unlocked state by manipulating a lever.

13. The drill guide of claim 1, wherein the collar is configured to transition between the locked state and the unlocked state by manipulating a switch.

14. The drill guide of claim 1, wherein the collar is configured to transition between the locked state and the unlocked state by manipulating a knob.

15. The drill guide of claim 1, wherein actuation of a button is configured to compress a spring within the handle.

16. The drill guide of claim 1, wherein actuation of a button is configured to transitions the collar from the locked state to the unlocked state.

17. The drill guide of claim 16, wherein the button is generally aligned with a longitudinal axis of the handle.

18. A drill guide comprising:
    at least one drill guide lumen including a proximal opening, a distal opening, and a longitudinal opening therebetween;
    an elongate member including a first end coupled to the at least one drill guide lumen and a second end coupled to a coupling;
    a handle coupled to the at least one drill guide lumen and configured to slide within the coupling, the handle movable between a first position relative to the at least one drill guide lumen and a second position relative to the at least one drill guide lumen,
    wherein the first position comprises a first translational position of the handle relative to the at least one drill guide lumen and the second position comprises a second translational position of the handle relative to the at least one drill guide lumen.

19. The drill guide of claim 18, wherein the handle comprises one or more stops configured to abut the coupling.

20. The drill guide of claim 18, wherein the coupling surrounds the handle.

21. A method of positioning a drill guide lumen having a longitudinal axis, the method comprising:
- positioning at a treatment site a drill guide comprising a drill guide lumen coupled to an elongate member, the elongate member coupled to a bushing, the bushing surrounded b a collar, the collar comprising a flange, and the collar disposed within a handle;
- positioning the drill guide lumen with the handle in a first position;
- sliding the collar within the handle to disengage the flange from the bushing; and
- moving the handle from the first position to a second position while the drill guide lumen remains substantially stationary.

22. The method of claim 21, wherein moving the handle comprises rotating the handle from the first position to the second position.

\* \* \* \* \*